United States Patent
Porwancher (12)

(10) Patent No.: US 6,665,652 B1
(45) Date of Patent: Dec. 16, 2003

(54) METHOD OF DIAGNOSIS OF LYME DISEASE

(76) Inventor: Richard B. Porwancher, 601 Ewing St., Suite C-7, Princeton, NJ (US) 08540

( * ) Notice: Subject to any disclaimer, the term of this patent is extended or adjusted under 35 U.S.C. 154(b) by 0 days.

(21) Appl. No.: 09/626,854

(22) Filed: Jul. 27, 2000

Related U.S. Application Data

(60) Provisional application No. 60/198,411, filed on Apr. 19, 2000, and provisional application No. 60/146,004, filed on Jul. 28, 1999.

(51) Int. Cl.$^7$ .......................... G06F 17/00; G06F 9/44; G06N 7/02; G01N 33/563; G01N 33/564
(52) U.S. Cl. .............. 706/45; 706/52; 706/61; 706/900; 702/19; 436/506; 436/513; 436/811; 435/7.1
(58) Field of Search ................ 706/45, 52, 61; 702/19; 436/506, 513, 811; 435/7.1

(56) References Cited

U.S. PATENT DOCUMENTS

| | | | |
|---|---|---|---|
| 4,816,387 A | | 3/1989 | Osther |
| 6,076,083 A | * | 6/2000 | Baker .......................... 706/45 |

OTHER PUBLICATIONS

Blaauw et al. (J. Clin, Epidemiol. 1992, vol. 45, pp. 1229–1236).*

Porwancher, R. A reanalysis of IgM western blot criteria for the diagnosis of early Lyme disease. The Journal of Infectious Diseases, 1999, vol. 179, pp. 1021–1024.*

Fagan, T.J. Nomogram for Bayes's Theorem. New England Journal of Medicine, 1975, vol. 293, No. 5, p. 257.*

Moneta et al. A symbolic–neural classification system assisting the characterization of the Lyme–Disease. IEEE International Conference on Systems, Man and Cybernetics, IEEE Press, 1992, vol. 1 pp. 136–139.*

Plank, C. et al. Computer–based interpretation of Test Results in the Diagnostics of Lyme Borreliosis. J. Lab. Med. 1997, vol. 21 No. 5 pp. 267–272. (German Language Paper).*

Engstrom, et al., J. Clin. Microbiol., 33 (1995), Immunoblot Interpretation Criteria for Serodiagnosis of Early Lyme Disease, pp. 47–55.

Hilton, et al., Infect. Diseases in Clin. Practice, 3 (1994), Is history useful in the diagnosis of lyme borreliosis?, pp. 277–281.

Fawcett, et al., J. Rheumatol., 19:4 (1992), Frequency and Specificity of Antibodies that Crossreact with *Borrelia burgdorferi* Antigens., pp. 582–587.

Ledue, et al., J. Clinical Microbiol., 34:10 (1996), New Laboratory Guidelines for Serologic Diagnosis of Lyme Disease: Evaluation of the Two Test Protocol., pp. 2343–2350.

* cited by examiner

*Primary Examiner*—Mary K. Zeman
(74) *Attorney, Agent, or Firm*—Dechert LLP

(57) ABSTRACT

A method for diagnosing whether a patient has a disease comprising interpreting the results of an immunoassay, wherein the immunoassay is viewed as a series of separate tests performed in parallel. The immunoassay can be a Western blot and the disease can be Lyme Disease.

26 Claims, 2 Drawing Sheets

METHOD OF DIAGNOSIS OF LYME DISEASE

The present application claims priority from Provisional Application No. 60/146,004 filed Jul. 28, 1999 and provisional application No. 60/198,411, filed Apr. 19, 2000.

The present invention relates to an improved method for the diagnosis of diseases and, in particular, infectious diseases such as Lyme Disease. A mathematical algorithm using Bayesian analysis is applied to data derived from an immunoassay such as a Western blot, Southern blot, an immunodot or other immunoassay technique. By combining the clinician's estimate of the pretest likelihood of disease with the immunoassay results through this specific algorithm, a more accurate diagnosis can be made. This algorithm is equally valid for any disease which is diagnosed using multiple immunoassays performed in parallel and where the antigens detected by these assays produce an antibody response in controls that is independent of one another.

In the last several years, Lyme Disease has become an increasing public health concern, for example, in the Northeast and upper Midwest regions of the United States (Morb Mortal Wkly Rep. 1994;43:564–572). Lyme Disease is a multisystem infectious disease caused by the spirochete *Borrelia burgdorferi*. This spirochete is transmitted by the bite of the tick *Ixodes scapularis*, often found on white-tailed deer. Lyme Disease ordinarily begins with flu-like symptoms such as headache, chills, joint pain, nausea and fatigue. An expanding rash called erythema migrans is characteristic of this disorder in the early stages, often beginning at the site of the tick bite. "Early stage" or "early" Lyme Disease is the four (4) week period following onset of symptoms. "Late stage" or "late" Lyme Disease is the period beyond early stage. Early stage Lyme Disease is most often curable with antibiotics. However, if left untreated or undiagnosed, Lyme Disease can cause serious complications including meningitis, chronic arthritis, encephalitis, peripheral nerve damage and even cardiac abnormalities. Although often treatable, sometimes these complications may be permanent and therefore accurate and early diagnosis is imperative.

The diagnosis of Lyme Disease has, however, proved problematic. In the past, the diagnosis of Lyme Disease had been based mainly on clinical symptomatology, not laboratory tests, since culture or visualization of the spirochete *Borrelia burgdorferi* from patient specimens was infrequent, and serologic tests were just being developed. Clinicians placed emphasis on the history of a tick bite, the observation of the characteristic erythema migrans rash and the presence of typical physical signs such as arthritis or Bell's Palsy, a neurologic condition. In recent times it has been realized that only 60–80% of patients with Lyme Disease have a rash, only 33–50% recall a tick bite, and that atypical presentations of the disease are now being recognized, thus making laboratory diagnosis more important. However, currently available blood tests for Lyme Disease, for example, enzyme-linked methods such as ELISA or immunofluorescent (IFA) methods, have been known to produce both false-negative and false-positive results. False-negative results have been seen frequently in early and sometimes in late Lyme Disease. False-positive results have been seen in some normal adults and in patients with certain specific conditions such as syphilis, Epstein-Barr viral infection, and connective tissue disorders such as rheumatoid arthritis or systemic lupus erythematosus. For example, among patients seen in Lyme Disease specialty clinics in the Northeast United States, only 6–34% of those with positive serology by an ELISA method were confirmed to have active Lyme Disease. Reproducibility of results between laboratories had been poor and standardization of reagents and interpretative standards had been lacking. These serious limitations prompted the Centers for Disease Control and the Association of State and Territorial Public Health Laboratory Directors to convene the Second National Conference on Serologic Diagnosis of Lyme Disease in October, 1994. At this conference a two-step procedure for diagnosing Lyme Disease was proposed consisting of an initial screening assay by an ELISA or IFA method followed by confirmatory Western blotting for all specimens found to be positive or equivocal by the initial screening test. Negative screening tests would obviate the need for further testing. In addition, standardization of reagents and interpretive standards were proposed. This conference established the role of the Western blot test as a means of improving the specificity of Lyme serologic testing.

The Western blot technique involves separating borrelial proteins by polyacrylamide gel electrophoresis and then transferring these proteins electrophoretically (blotting) to a nitrocellulose membrane or chemically treated paper. These proteins generally will bind to the membrane or paper in a pattern identical to that in the gel. Bands of antigen (bound to the paper or membrane) can be detected visually by overlaying the blot with the patient's serum followed by an anti-immunoglobulin antibody. Both IgG and IgM type antibodies can be detected by the Western blot technique. In a typical patient with Lyme disease the initial response of the patient's body is to make IgM antibody within the first few weeks of the infection, followed shortly thereafter by an IgG antibody response. Both the number and type of bands identified in the Western blot technique are useful in distinguishing patients who have Lyme Disease from normal control patients and patients with other diseases. Western blots are also referred to as "Western immunoblots". Interpretive standards proposed by the Centers for Disease Control and Prevention (CDC) were based on studies by Dressler et al., J. Infect. Dis. 1993; 167:392–400, Engstrom et al., and J. Clin. Microbiol. 1995; 33:419–27. According to the CDC, a positive IgM Western blot required identification of any two of the following bands: 23, 39, or 41 kilodaltons and a positive IgG Western blot required identification of any five of the following ten bands: 18, 21, 28, 30, 39, 41, 45, 58, 66 or 93 kilodaltons. Either IgG or IgM Western blots were recommended by the CDC for diagnosis of early Lyme Disease, whereas only IgG Western blotting is recommended for diagnosis of late Lyme Disease.

After the CDC proposed the above criteria, problems with both sensitivity and specificity of the test results were appreciated. A study by Aguero-Rosenfeld et al., J. Clin. Microbiol. 1996; 34:1–9 evaluated the serologic response of patients with culture-confirmed early Lyme Disease using the CDC criteria and found that only 43% had a positive IgM Western blot and only 22% had a positive IgG Western blot by these standards. If CDC guidelines are followed, then failure to confirm screening tests by IgG or IgM Western blot will likely result in undertreating some patients who have Lyme Disease. In addition, the current criteria fail to consider the influence of the pre-test likelihood of disease on the interpretation of the test results. It can be predicted that Western blot testing will yield some false positive results when applied to a population where Lyme Disease is uncommon or when typical signs and symptoms are lacking. Sivak et al., Arch. Intern. Med. 1996; 156:2105–9, recently published a Bayesian analysis of IgM Western blotting for the diagnosis of early Lyme Disease and concluded that the accuracy would be poor in patients with minimal clinical evidence for Lyme Disease. Based on the currently available technology and using CDC criteria for interpretation, patients will continue to be undertreated and overtreated for Lyme Disease.

In a presentation by Porwancher, an incorrect algorithm was employed which led to an erroneous estimation of the probability of disease. (Thirty-fifth Annual Meeting, Infectious Disease Society of America, San Francisco, Sep. 14, 1997 (Abstract 247), see Clinical Infectious Diseases August, 1997.)

Given the above background, there remains a need for improved methods for diagnosing Lyme Disease. The present invention provides a method of interpreting Western blot results by combining the pre-test likelihood of disease as estimated by the patient's clinician with the patient's specific Western blot band pattern through a mathematical algorithm, thus deriving the post-test probability of Lyme Disease for that patient. This invention may be used for the diagnosis of any infectious disease where multiple immunoassays are performed in parallel.

SUMMARY OF THE INVENTION

A method for determining that a subject has a disease when multiple immunoassay tests are performed in parallel.

DETAILED DESCRIPTION OF THE INVENTION

Figure 1:
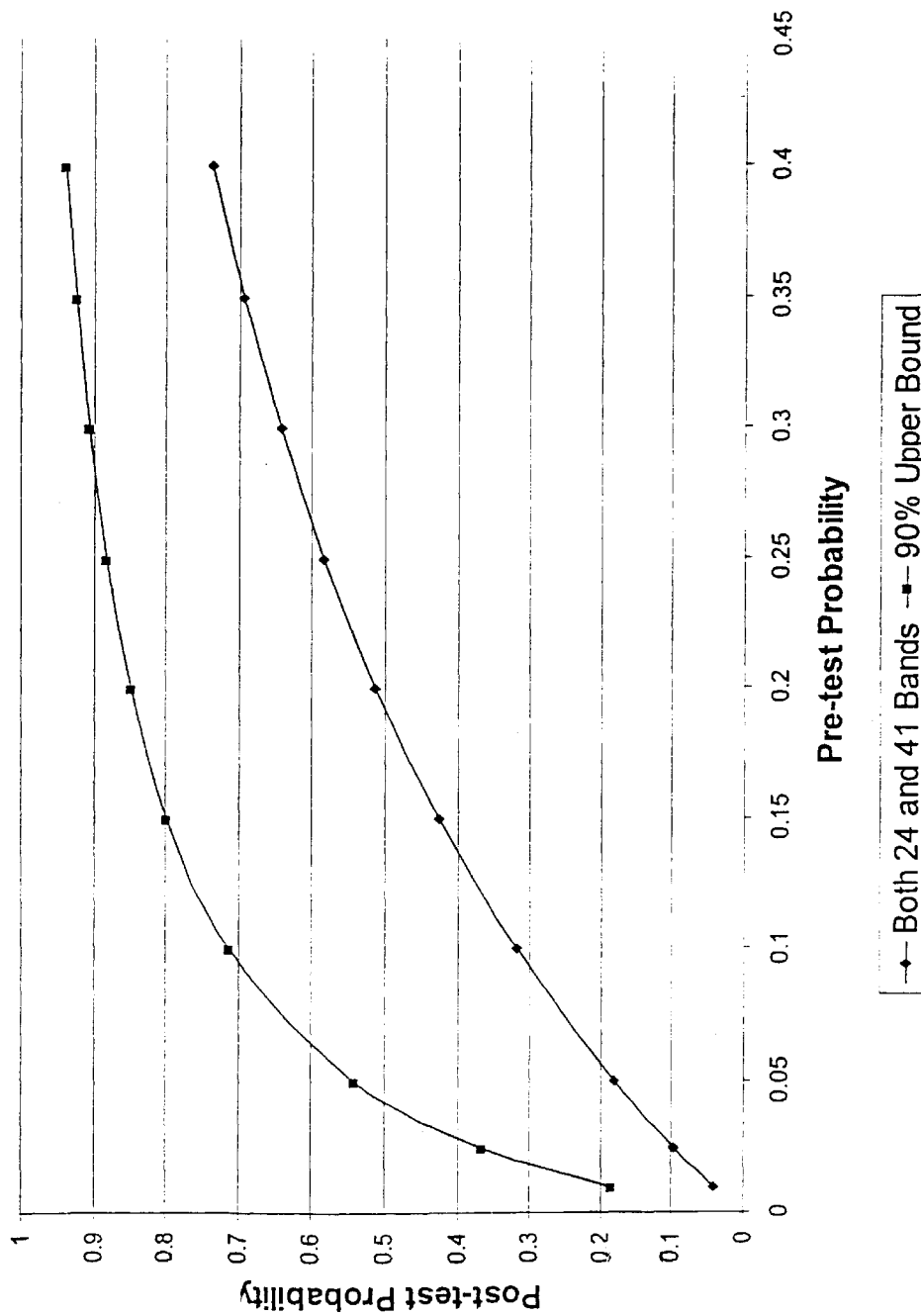
FIG. 1 is a graph depicting the relationship between pre-test probability of Lyme Disease based on the physician's clinical estimate and the post test probability of Lyme Disease using the IgM Western blot.

The present invention is directed to a method of evaluating the likelihood of a patient having a particular disease by employing (i) placing a numerical value on the signs and symptoms presented by a subject (the "patient point scale"), (ii) determining the pretest likelihood that the patient has the disease, (iii) if indicated, running one or more diagnostic tests for the disease, (iv) analyzing the results of the diagnostic tests (the "post test evaluation"), and (v) employing the patient point scale and the post test evaluation to determine the probability that the patient does have the disease. The presence of additional conditions, referred to herein as an "extra condition," such as the results of an additional test such as ELISA or IFA, or the vaccination of a subject, for example, with the Lyme Disease vaccine, leads to a conditional probability which is employed in a method of the present invention. The pretest probability of disease is estimated from the specific clinical signs and symptoms of the patient and by comparing these findings with descriptions of disease published in the medical literature. For example, based on reports published from Lyme Disease clinics in the Northeast United States where the disease is endemic, the prevalence of Lyme Disease has ranged from 1% in patients who are self-referred to 40% in patients who are physician-referred. Although these results may seem surprisingly low, they emphasize the lack of specificity of patient complaints. If a physician familiar with Lyme Disease diagnoses the typical rash called erythema migrans, then no further testing is ordinarily required. However, physician confirmation of the rash is not always possible and it is often necessary to rely on the patient's description of the rash as well as other signs and symptoms of Lyme Disease. Several studies have compared specific signs and symptoms in patients with Lyme Disease to normal control patients from endemic areas and to patients evaluated at Lyme clinics but later determined not to have Lyme Disease. Using Chi-squared analysis (2×2 contingency tables, $p<0.05$) Hilton et al. identified joint pain, concentration difficulties, and Bell's palsy as predictive of Lyme Disease compared to non-Lyme controls. Shadick et al. (1994) compared signs and symptoms in patients with Lyme Disease to normal control patients living in the same endemic area. Symptoms statistically associated with Lyme Disease included joint pain, numbness in an extremity, and memory loss. Using multivariate analysis, joint symptoms and neurologic symptoms were found to be independent predictors of Lyme Disease. A deer tick bite has been associated with a 5% risk of disease in highly endemic areas (Blaauw et al., 1992, Magid et al., 1992). Patient confirmed erythema migrans (identified by photograph) has been found to have a 15% positive predictive value (Blaauw et al., 1992). Thus, it is clear that risk factors for Lyme Disease have been identified, aiding the physician in estimating the likelihood of clinical disease. However only a few published studies exist which help clinicians estimate the pre-test probability of Lyme Disease [Huppertz et al. (1998), Blaauw et al. (1993)]. Conducted in Europe these studies address Lyme arthritis but not other manifestations of the disease. Data is herein presented from a Lyme Disease clinic in the Northeast U.S. regarding the use of scored clinical criteria for estimating the pre-test probability of Lyme Disease. A patient point scale is provided to estimate the pretest risk of Lyme Disease is set forth in Table 1:

TABLE 1

PATIENT POINT SCALE FOR LYME DISEASE

Setting a) Exposure to wooded, brushy, or grassy areas in a county in which Lyme Disease has been commonly diagnosed (Add 4 points).

Signs a) Asymmetric, unexplained pauciarticular arthritis, often relapsing.
b) Unexplained, acute onset high-grade atrioventricular cardiac conduction defects.
c) Unexplained Bell's palsy, peripheral neuropathy, or radiculopathy.
d) Aseptic meningitis or encephalitis.
(Add 6 points for each of the above categories present).

Symptoms a) Patient-confirmed Erythema migrans: Expanding round or elliptical rash at least five cm. in diameter, sometimes multiple, often with central clearing, starting 3–30 days following a tick bite. Identification by photographic example preferred. (Add 6 points).
b) Deer tick bite. (Add 2 points)
c) Generalized arthralgias or myalgias (Add 1 point)
d) Distal extremity parethesias, concentration difficulty, or memory loss. (Add 1 point)
e) Headache plus either fever or neck stiffness. (Add 1 point)

Interpretation 14 or more points: High probability of Lyme Disease (64%)
7–13 points: Moderate probability of Lyme Disease (19%)
≦6 points: Lower probability of Lyme Disease (7%)

The interpretation of the patient point scale for Lyme Disease is based on empirical data described below. Although the lower probability of Lyme Disease is given at 7%, the interpretation of the value is a probability of no more than 7%. A patient point scale for other diseases can be developed employing the same methodology adopted for the particular disease.

Two separate studies conducted in New Jersey were used to evaluate scored clinical criteria of the patient point score of Table 1 in a retrospective fashion. These studies will be described separately.

Study 1

Patient population. All adults and children evaluated at a central New Jersey community teaching hospital Lyme Disease clinic from November 1996 through December 1997 were included in this study. Patients were both physician-referred and self-referred.

Study procedures. All patients underwent a complete history examination and completed an extensive questionnaire about Lyme Disease-related symptoms. Patients were asked to identify any self-reported erythema migrans rash by reviewing photographs and estimating the size of the rash in centimeters. Charts were retrospectively and independently reviewed by two investigators, one of whom was unfamiliar with the study patients. Signs and symptoms had to be present within six months of the initial clinic evaluation to be considered part of the current illness. Patients were designated as having definite Lyme Disease if they met the Centers for Disease Control and Prevention case surveillance definition MMWR 1990; 39 (RR-13):19–21 with one modification-encephalitis was defined as cognitive deficits leading to impaired function both at home and at work associated with abnormal cerebrospinal fluid analysis, elevated intracranial pressure, or intrinsic cerebrospinal fluid Lyme Disease antibody production. Peripheral nervous system disease was confirmed by either an abnormal physical examination or neurophysiologic testing. Seroconversion was also accepted as proof of definite Lyme Disease. Probable Lyme Disease was defined as an influenza-like illness (e.g. fever, headache, neck stiffness, arthralgias, and myalgias) confirmed by both enzyme immunoassay (EIA) and Western blot for Lyme Disease and by a favorable response to antibiotics. In the event of a disagreement between investigators, a third investigator unfamiliar with the study patients evaluated the case record to produce a majority decision. A research nurse unfamiliar with the study patients and blinded to disease category reviewed the medical record for signs and symptoms listed in Table 1 to produce an individual patient score.

Scored Clinical Criteria. Patients with investigator-documented erythema migrans had their signs and symptoms recorded but were not scored. The scored clinical criteria listed in Table 1 were modeled after the CDC surveillance definition MMWR 1990; 39 (RR-13):19–21. The criteria in this study included the prevalence of Lyme Disease in the community, rheumatologic, cardiac, peripheral nervous system, and central nervous system signs, patient-reported erythema migrans, tick bite, rheumatologic symptoms, neurologic symptoms, and constitutional symptoms such as fever and headache. In order to be used for a pretest clinical score, the definition of encephalitis could not include serologic confirmation and was therefore defined as cognitive deficits resulting in impaired function at home and at work. Unless non-ambulatory, all patients were automatically credited with 4 points for outdoor exposure in a Lyme-endemic community. The weight assigned each criterion was largely empiric although guided by likelihood ratios reported in the literature. Hilton et al. (Infect. Dis. Clin. Pract. 1994; 3:277–81) and Shadick et al. (Ann. Intern. Med. 1994; 121:560–7) both confirmed arthralgias as a weak predictor of Lyme Disease with likelihood ratios of 1.3 and 3.8 respectively. Because Hilton et al. used controls derived from their own clinic population, the lower likelihood value was felt to be more applicable to patients presenting to their physician for evaluation. Similarly, a likelihood ratio of 1.4 was associated with concentration difficulty (see Hilton, et al.). Both arthralgias and concentration difficulties were assigned one point each in the clinical score. Points assigned to other criteria were based on multiples of this base likelihood ratio. Tick bite was noted to have a likelihood ratio of 2.0–3.6 Huppertz et al., Eur. J. Pediatr. 1998; 157:304–8; Blaauw, et al., J. Clin. Epidemiol. 1992; 45:1229–36 and patient-reported erythema migrans a ratio of 8.5 (Blaauw, et al. 1992). The latter ratio represents the lowest end of the 95% confidence interval for this criterion in the study by Blaauw et al. 1992. Huppertz et al. 1998 suggested that episodic arthritis (likelihood ratio 4.8) and arthritis involving the knee in children (likelihood ratio 1.6) independently contributed to the diagnosis of Lyme Disease, leading us to estimate that episodic, pauciarticular arthritis would be associated with a likelihood ratio of 7.7. Peripheral neurologic signs were associated with a likelihood ratio of 4.1 from a study by Steere et al., JAMA, 1993; 269:1812–6. Data from Hilton et al. 1994 suggests a likelihood ratio of 2.75 for Bell's palsy. In another study, the presence of meningitis combined with isolated cranial neuropathy was associated with a likelihood ratio of 10.8, Kindstrand, J. Neurol., 1995; 242:658–63. In addition to using likelihood ratios generated from the literature, data was also generated from the current study regarding likelihood ratios for erythema migrans, fever, Bell's palsy, and meningitis. The remainder of the category weights represent the author's best estimates. If a given patient had clinical signs of disease, additional points were not added for symptoms referable to the same affected organ system (e.g. arthralgias were not considered in the score when credit was already given for arthritis).

Statistical Analysis. Including data from all study patients, univariate analysis was performed for all sign and symptom categories and individually for headache, fever, and neck stiffness by chi-squared. Multivariate logistic regression analysis was performed to evaluate the interaction of variables with p-values<0.20 by univariate analysis. For patients without investigator-documented erythema migrans, the weighted scores of patients with and without Lyme Disease were compared using the t-test, and a logistic regression of disease category (Lyme Disease versus non-Lyme Disease) on score was performed.

Study 2

Patient population. Both adults and children were referred to one of three New Jersey medical centers for a prospective clinical and serologic study of neuroborreliosis. Children with encephalitis and persons previously treated for Lyme Disease with parenteral antibiotics within two years of evaluation were excluded from the study.

Study procedures. Institutional review board approval of the study protocol and consent form was obtained at each participating institution. After obtaining informed consent, patients underwent a complete history and physical examination and laboratory studies including a complete blood count, routine chemistries, urinalysis, cerebrospinal fluid analysis, rapid plasma reagin testing, thyroid function tests, serum Lyme Disease IgG Western blot, and both serum and cerebrospinal fluid Lyme serology by antibody-capture enzyme immunoassay for IgG, IgM, and IgA type antibodies. Although some patients had Lyme serologic testing by outside laboratories, all serology was confirmed by a single reference laboratory. Encephalitis patients underwent formal neuropsychiatric testing upon enrollment and again two months after treatment. Subjects completed the MMPI-2, the Weschler Adult Memory Scales (First Edition), and the WAIS-R. Patients were followed a minimum of two months after enrollment. A research nurse unfamiliar with the study patients and blinded to disease category reviewed the medical record for signs and symptoms listed in Table 1 to produce an individual patient score. Signs and symptoms needed to be present within six months of the initial evaluation to be considered part of the current illness. Disease categorization was determined by a majority vote of the three principal investigators, blinded to the clinical score. Patients with definite neuroborreliosis needed to satisfy the CDC surveillance definition and have positive serology by all testing laboratories. Probable Lyme Disease patients met the CDC surveillance definition, but had serology which was not reproducible between laboratories. All other patients were assigned to the non-Lyme Disease category.

Univariate analysis was performed for all signs and symptoms recorded by chi-squared with Yates' correction ($2 \times 2$ contingency tables, $p<0.05$) or Fisher's exact test. A logistic regression of disease category on score was also performed for patients without investigator-documented erythema migrans.

Results

Seventy-four consecutive patients were evaluated during the first study. Seventeen patients (23%) had Lyme Disease according to the study criteria, and included 10 definite and 7 probable cases. Investigator concordance for disease category (definite and probable Lyme vs. non-Lyme) was 92%. Among definite Lyme Disease patients, three had arthritis, two had investigator-confirmed erythema migrans, two had encephalitis, two had Bell's palsy, and one had an influenza-like illness with seroconversion. Of the seven probable cases, none had clinical or laboratory evidence to suggest a diagnosis of Ehrlichosis. Among patients with neuroborreliosis, seven had meningitis, seven had Bell's palsy, four presented with Erythema migrans, two had peripheral neuropathy, and one had encephalitis. Investigator concordance for disease category. (definite and probable Lyme vs. non-Lyme) was 85%.

Univariate analysis of the first study identified Erythema migrans, and fever as risk factors for Lyme Disease. Similar analysis of the prospective neuroborreliosis study identified Erythema migrans, Bell's palsy, and aseptic meningitis as risk factors. Combining data from both studies yielded likelihood ratios of 7.7 for Bell's palsy, 16.6 for aseptic meningitis, 11.8 for patient-confirmed erythema migrans, and 2.0 for fever.

Multiple logistic regression analysis of the variables in the first study revealed that fever was no longer a significant predictor of disease, but headache became a significant variable. Erythema migrans remained significant, particularly when combined with headache ($R^2=0.1587$, $p<0.0001$). Adding either fever or tick bite to the combination of erythema migrans and headache improved the results slightly ($R^2=0.1774$, $p<0.0001$).

After excluding patients with investigator-documented erythema migrans, significant differences in clinical scores were found between Lyme and non-Lyme patients in both studies. Using data from the retrospective study, the average scores were 11.73 and 7.68 for Lyme and non-Lyme patients, respectively (t-Test 3.554, $p=0.0007$). Scores from the neuroborreliosis study were 15.30 and 8.21 for Lyme and non-Lyme patients, respectively (t-Test 4.512, $p<0.0002$).

Using data from Study 1, a logistic regression of disease on clinical score revealed an $R^2=0.1398$, $p<0.0001$. For patients with scores $\leq 6$, the risk of Lyme Disease was 7% (95% CI: 0–21%), for those with scores 7–13, the risk of Lyme Disease was 19% (95% CI: 11–26%), and for those with scores $\geq 14$, the risk of Lyme Disease was 64% (95% CI: 36–91%). However, a similar analysis using data from the neuroborreliosis study revealed an $R^2=0.4371$, $p<0.001$. Although useful for both patient populations, the point scale was a more effective predictor of neuroborreliosis.

Once the pre-test likelihood of disease has been estimated by the physician, by using the patient point score, a determination is made as to whether to proceed with a diagnostic test such as the ELISA or Western blot. Western blot gels are available through several sources (e.g., MarDx Diagnostics Inc., Carlsbad, Calif.). The performance characteristics of each commercial source for Western blots for both IgG and IgM antibodies are established in patients with Lyme Disease and in control patients with either positive or negative screening ELISA serology as determined by the manufacturer. Band frequencies are established in normal healthy control patients living in non-endemic areas. Next, differences in the band frequencies between Lyme Disease patients and controls are determined using Chi-squared analysis ($2 \times 2$ contingency tables, $p \leq 0.01$). From this analysis, specific Western blot IgG and IgM bands associated with Lyme Disease can be identified. The frequency of positive bands on Western blot tests has been shown to be related to the ELISA status of the patient (Engstrom et al., 1995)—i.e., patients with positive ELISA screening tests are more likely to have bands present by Western blot. Since both ELISA and Western blot testing are often performed routinely for screening purposes by commercial laboratories, the results of the ELISA test performed on a given patient's serum can be included at the time the band frequencies for the Western blot analysis are chosen. The frequency of each Western blot band pattern associated with a Disease ("L") such as Lyme Disease can be determined by studying groups of patients with the disease—both ELISA-positive and ELISA-negative. For patients with Lyme Disease, patients with early and late Lyme Disease are studied separately. See Porwancher, J. Infect. Dis., April, 1999.

From a mathematical perspective, an immunoassay such as Western blot may be viewed as a series of separate tests performed in parallel, some with positive and others with negative results. The posttest probability that a given Western blot pattern represents a Disease ("L") such as Lyme Disease may be computed by the formula: Given i, j, k$\in J$ of size n, but i$\neq$k, P(L) is the prior probability of Lyme Disease, $P(B_j/L)$ is the probability of the jth Western blot band, $B_j$, given Lyme Disease is present; $B_1 B_2 = B_1 \cap B_2$, $P(B_j) \neq 0$, $L \cap B_j \neq \emptyset$, and $P(B_j/L)$ is significantly greater than $P(B_j/L')$ ($P \leq 0.01$ for each j$\in J$); then $$\frac{P(B_i \ldots B_j B'_{j+1} \ldots B'_n / L) \times P(L)}{P(B_i \ldots B_j B'_{j+1} \ldots B'_n / L) \times P(L) + \left[\prod_{i=1}^{j} P(B_i / L')\right] \times \left[\prod_{k=j+1}^{n} P(B'_k / L')\right] \times P(L')}$$

wherein:

$B_1, \ldots, B_n$ represents a group of bands seen in the Western blot which are associated with infection with Lyme Disease, and tested for by Western blot for a given patient;

$B_1, \ldots, B_j$ represents those bands included in $B_1, \ldots, B_n$ which are present in the results of a given Western blot;

$B'_{j+1}, \ldots, B'_n$ represents those bands included in $B_1, \ldots, B_n$ which are not present in the results of a given Western blot;

$P(B_1 \ldots B_j B'_{j+1} \ldots B'_n/L)$ represents the frequency that a given Western blot pattern is present in patients with Lyme Disease;

$P(L)$ represents the pre-test probability of infection with Lyme Disease;

$P(B_i/L')$ represents the frequency with which a band, $B_i$, appears in Western blots when there is no infection with Lyme Disease;

$$\left[\prod_{i=1}^{j} P(B_i/L')\right]$$

represents the product of the frequencies with which the individual bands present in the immunoblot pattern appear in Western blots when there is no infection with Lyme Disease;

$P(B'_k/L')$ represents the frequency with which a band, $B_k$, is absent in Western blots when there is no infection with Lyme Disease ($i \neq k$);

$$\left[\prod_{k=j+1}^{n} P(B'_k/L')\right]$$

represents the product of the frequencies with which the individual bands not present in the immunoblot pattern are absent in Western blots when there is no infection with Lyme Disease;

$P(L)$ can be determined using a patient point score;

$P(L')$ represents a pre-test probability of no infection with Lyme Disease; and $P(L')=1-P(L)$.

$P(B_1 \ldots B_j B'_{j+1} \ldots B'_n/L)$ can be determined by studying the Western blot patterns of patients confirmed to have Lyme Disease.

When a specific band pattern is not part of an existing data set, then we can estimate that $P(B_1 \ldots B_j B'_{j+1} \ldots B'_n/L)$ is less than or equal to $P(B_m/L)$, where $P(B_m/L)$ represents the smallest of $P(B_i/L)$ where $i=1, 2, \ldots, j$ and $P(B'_k/L)$ where $k=j+1, \ldots, n$, and $i \neq k$, and $P(B_1 \ldots B_j B_{j+1}' \ldots B'_n/L)$ is greater than or equal to $$\left[\prod_{i=1}^{j} P(B_i/L)\right] \times \left[\prod_{k=j+1}^{n} P(B'_k/L)\right]$$

This algorithm is equally valid for any disease (L) which is diagnosed using multiple immunoassays performed in parallel and where the antigens detected by these immunoassays produce an antibody response in controls that is independent of one another.

Late Lyme Disease

The post test probability that the results of a given Western blot indicates infection with Lyme Disease is determined using the formula:

Given $i$, $j$, $k \in J$ of size $n$, but $i \neq k$, $P(L)$ is the prior probability of Lyme Disease, $P(B_j/L)$ is the probability of the jth Western blot band, $B_j$, given late Lyme Disease is present; $B_1 B_2 = B_1 \cap B_2$, $P(B_j) \neq 0$, $L \cap B_j \neq \emptyset$, and $P(B_j/L)$ is significantly greater than $P(B_j/L')$ ($P \leq 0.01$ for each $j \in J$); then $$\frac{P(B_l \ldots B_j B'_{j+1} \ldots B'_n/L) \times P(L)}{\begin{array}{c} P(B_l \ldots B_j B'_{j+1} \ldots B'_n/L) \times \\ P(L) + \left[\prod_{i=1}^{j} P(B_i/L')\right] \times \left[\prod_{k=j+1}^{n} P(B'_k/L')\right] \times P(L') \end{array}}$$

wherein:

$B_1, \ldots, B_n$ represents a group of bands seen in the Western blot which are associated with infection with late Lyme Disease, and tested for by Western blot test for a given patient;

$B_1, \ldots, B_j$ represents those bands included in $B_1, \ldots, B_n$ which are present in the results of a given Western blot;

$B'_{j+1}, \ldots, B'_n$ represents those bands included in $B_1, \ldots, B_n$ which are not present in the results of a given Western blot;

$P(B_1 \ldots B_j B'_{j+1} \ldots B'_n/L)$ represents the frequency that a given Western blot pattern is present in patients with late Lyme Disease;

$P(L)$ represents the pre-test probability of infection with Lyme Disease;

$P(B_i/L')$ represents the frequency with which a band, $B_i$, appears in Western blots when there is no infection with Lyme Disease;

$$\left[\prod_{i=1}^{j} P(B_i/L')\right]$$

represents the product of the frequencies with which the individual bands present in the immunoblot pattern appear in Western blots when there is no infection with Lyme Disease;

$P(B'_k/L')$ represents the frequency with which a band, $B_k$, is absent in Western blots when there is no infection with Lyme Disease;

$$\left[\prod_{k=j+1}^{n} P(B'_k/L')\right]$$

represents the product of the frequencies with which the individual bands not present in the immunoblot pattern are absent in Western blots when there is no infection with Lyme Disease;

$P(L)$ can be determined using a patient point score;

$P(L')$ represents a pre-test probability of no infection with Lyme Disease; and $P(L')=1-P(L)$.

$P(B_1 \ldots B_j B'_{j+1} \ldots B'_n/L)$ can be determined by studying the Western blot patterns of patients confirmed to have late Lyme Disease.

When a specific band pattern is not part of an existing data set, then we can estimate that $P(B_1 \ldots B_j B'_{j+1} \ldots B'_n/L)$ is less than or equal to $P(B_m/L)$, where $P(B_m/L)$ represents the smallest of $P(B_i/L)$ where $i=1, 2, \ldots, j$ and $P(B'_k/L)$ where k=j+1, ..., n, and i≠k, and P(B₁ ... BjB$_{j+1}$' ... B'$_n$/L) is greater than or equal to $$\left[\prod_{i=1}^{j} P(B_i/L)\right] \times \left[\prod_{k=j+1}^{n} P(B'_k/L)\right]$$

Early Lyme Disease

The post test probability that the results of a given Western blot indicate infection with early Lyme Disease using the formula:

Given i, j, k∈𝒥 of size n, but i≠k, P(L) is the prior probability of Lyme Disease, P(B$_j$/L) is the probability of the jth Western blot band, B$_j$, given early Lyme Disease is present; B₁B₂=B₁∩B₂, P(B$_j$)≠0, L∩B$_j$≠∅, and P(B$_j$/L) is significantly greater than P(B$_j$/L') (P≦0.01 for each j∈J); then $$\frac{P(B_l ... B_jB'_{j+1} ... B'_n/L) \times P(L)}{P(B_l ... B_jB'_{j+1} ... B'_n/L) \times P(L) + \left[\prod_{i=1}^{j} P(B_i/L')\right] \times \left[\prod_{k=j+1}^{n} P(B'_k/L')\right] \times P(L')}$$

wherein:

- B₁, ..., B$_n$ represents a group of bands seen in the Western blot which are associated with infection with early Lyme Disease, and tested for by Western blot test for a given patient;
- B₁, ..., B$_j$ represents those bands included in B₁, ..., B$_n$ which are present in the results of a given Western blot;
- B'$_{j+1}$, ..., B'$_n$ represents those bands included in B₁, ..., B$_n$ which are not present in the results of a given Western blot;
- P(B₁ ... B$_j$B'$_{j+1}$ ... B'$_n$/L) represents the frequency that a given Western blot pattern is present in patients with early Lyme Disease;
- P(L) represents the pre-test probability of infection with Lyme Disease;
- P(B$_i$/L') represents the frequency with which a band, B$_i$, appears in Western blots when there is no infection with Lyme Disease;

$$\left[\prod_{i=1}^{j} P(B_i/L')\right]$$

represents the product of the frequencies with which the individual bands present in the immunoblot pattern appear in Western blots when there is no infection with Lyme Disease;

P(B'$_k$/L') represents the frequency with which a band, B'$_k$, is absent in Western blots hen there is no infection with Lyme Disease;

$$\left[\prod_{k=j}^{n} P(B'_k/L')\right]$$

represents the product of the frequencies with which the individual bands not present in the immunoblot pattern are absent in Western blots when there is no infection with Lyme Disease;

P(L) can be determined using a patient point score;

P(L') represents a pre-test probability of no infection with Lyme Disease; and

P(L')=1−P(L).

P(B₁ ... B$_j$B'$_{j+1}$ ... B'$_n$/L) is determined through a study of Western blot band patterns in patients with early Lyme Disease.

When a specific band pattern is not part of in an existing data set, then we can estimate that P(B₁ ... B$_j$B'$_{j+1}$ ... B'$_n$/L) is less than or equal to P(B$_m$/L), where P(B$_m$/L) represents the smallest of P(B$_i$/L) where i=1, 2, ..., j and P(B'$_k$/L) where k=j+1, ..., n, i≠k, and P(B₁ ... B$_j$B$_{j+1}$' ... B'$_n$/L) is greater than or equal to $$\left[\prod_{i=1}^{j} P(B_i/L)\right] \times \left[\prod_{k=j+1}^{n} P(B'_k/L)\right].$$

Lyme Disease With Extra Condition

A method for determining the post test probability that the results of a given Western blot indicates infection with Lyme Disease, when an extra condition is present, using the following formula:

Given i, j, k∈𝒥 of size n, but i≠k, P(L) is the prior probability of Lyme Disease, P$_E$(B$_j$/L) is the probability of the jth Western blot band, B$_j$, given Lyme Disease and the extra condition are present; B₁B₂=B₁∩B₂, P$_E$(B$_j$)≠0, L∩B$_j$≠∅, and P$_E$(B$_j$/L) is significantly greater than P$_E$(B$_j$/L') (P≦0.01 for each j∈J); then $$\frac{P_E(B_1 ... B_jB'_{j+1} ... B'_n/L) \times P(L)}{P_E(B_1 ... B_jB'_{j+1} ... B'_n/L) \times P(L) + \left[\prod_{i=1}^{j} P_E(B_i/L')\right] \times \left[\prod_{k=j+1}^{n} P_E(B'_k/L')\right] \times P(L)}$$

where P$_E$( ) represents the probability of the bracketed factor when the extra condition is present;

- B₁, ..., B$_n$ represents a group of bands seen on the Western blot which are associated with infection with Lyme Disease, and tested for by Western blot for a given patient;
- B₁, ..., B$_j$ represents those bands included in B₁, ..., B$_n$ which are present in the results of a given Western blot;
- B'$_{j+1}$, ..., B'$_n$ represents those bands included in B₁, ..., B$_n$ which are not present in the results of a given Western blot;
- P$_E$(B₁ ... B$_j$B'$_{j+1}$ ... B'$_n$/L) represents the frequency that the given Western blot pattern is present in patients with Lyme Disease and the extra condition;
- P(L) represents a pre-test probability of infection with Lyme Disease;
- P$_E$(B$_i$/L') represents the frequency with which a band, B$_i$, appears in Western blots when there is no infection with Lyme Disease but the extra condition is present;

$$\left[\prod_{i=1}^{j} P_E(B_i/L')\right]$$

represents the product of the frequencies with which the individual bands present in the immunoblot pattern appear in Western blots when there is no infection with Lyme Disease but the extra condition is present;

$P_E(B'_k/L')$ represents the frequency with which a band, $B_k$, is absent in Western blots when there is no infection with Lyme Disease but the extra condition is present;

$$\left[\prod_{k=j+1}^{n} P_E(B'_k/L')\right]$$

represents the product of the frequencies with which the individual bands not present in the immunoblot pattern are absent in Western blots when there is no infection with Lyme Disease but the extra condition is present;

P(L) is determined by a patient point score;

P(L') represents a pre-test probability of no infection with Lyme Disease; and

P(L')=1−P(L).

$P_E(B_1 \ldots B_j B'_{j+1} \ldots B'_n/L)$ is determined through a study of Western blot band patterns in patients with Lyme Disease when the extra condition is present.

When a specific band pattern is not part of in an existing data set, then we can estimate that $P_E(B_1 \ldots B_j B'_{j+1} \ldots B'_n/L)$ is less than or equal to $P_E(B_m/L)$, where $P_E(B_m/L)$ represents the smallest of $P_E(B_i/L)$ where i=1, 2, . . . , j and $P(B'_k/L)$ where k=j+1, . . . , n, and i≠k, and $P_E(B_1 \ldots B_j B_{j+1}' \ldots B'_n/L)$ is greater than or equal to $$\left[\prod_{i=1}^{j} P_E(B_i/L)\right] \times \left[\prod_{k=j+1}^{n} P_E(B'_k/L)\right].$$

Band Independence

To test the assumption of band independence in healthy controls, the observed frequency of multiple false-positive bands was compared to the frequency predicted by assuming independence. (See Appendix I) The observed frequency was then compared with the expected frequency (extrapolated to the nearest whole number) by Chi-square with Yates's correction (2×2 contingency tables, P<0.05). Data from control groups from several studies were used to evaluate this independence assumption.

Results

From the study by Engstrom et al., the sensitivity and specificity of the 24-, 39-, and 41-kDa IgM bands at the time of the initial patient evaluation were 0.840/0.560, 0.840/0.933, and 0.680/0.907, respectively. The predicted frequency of multiple false-positive significant IgM Western blot bands in healthy controls was 7.12%. When these values are rounded to the nearest whole number, one might expect 5 of 75 control patients will be falsely positive. By observation, only 6 (8%) of 75 control subjects had ≧2 significant IgM bands—a result not statistically different from that predicted by assuming band independence.

Additional data was evaluated from control groups of Ledue et al. (13) and Dressler et al. (14) from non-Lyme endemic areas and from the CDC for a Lyme-endemic area (Trevejo RT, unpublished data). From the Ledue study, the 24-, 39-, and 41-kDa IgM bands had specificities of 0.895, 0,921, and 0.921, respectively. Because monoclonal antibodies to specific band epitopes were not available, the bands identified by Dressler et al. were not directly comparable to the other studies. Therefor, all significant IgM bands identified by Dressler et al. were used to evaluate the independence assumption. The 18-, 21-, 28-, 37-, 41-, 45-, 58-, and 93-kDa bands had specificities of 0.98, 0.96, 1.0, 0.99, 0.98, 0.99, 0.99, and 0.99, respectively. The expected-versus-observed frequencies of multiple false-positive IgM bands in controls were derived (see Table 2). Although the individual sample sizes were small, collectively these data support the use of the independence assumption for estimating the frequency of false-positive results in normal controls.

TABLE 2

Comparison of frequency of expected versus observed multiple IgM Western blot bands in control subjects.

| Study, date | Observed | Expected |
|---|---|---|
| Dressler et al. [12], 1993 | 1/125 | 1/125 |
| Engstrom, et al. [10], 1995 | 6/75 | 5/75 |
| Trevejo (unpublished data), 1998 | 1/38 | 1/38 |
| Ledue et al. [4], 1996 | 0/29 | 0/29 |

NOTE: P-value not significant, all studies.

Similar analysis was performed for IgG Western immunoblots collected from control patients from several studies (see Table 3).

TABLE 3

To compare predicted frequencies of 2 or more IgG bands occurring together in controls against observed frequencies for multiple IgG bands:

| Study (date) | Observed | Expected | P value |
|---|---|---|---|
| Fawcett et al. (1992) | 11/142 | 14/142 | NS |
| Hauser et al. (1997) | 3/141 | 2/141 | NS |
| Dressler et al. (1993) | 29/125 (est.) | 17/125 | >0.05 Chi-square 3.22 |
| Engstrom et al. (1995) | 3/75 | 3/75 | NS |
| Trevejo et al. (1998) | 6/38 | 8/38 | NS |
| Ledue et al. (1996) | 1/29 | 3/29 | 0.31 (NS) |

No significant difference was detected in observed versus expected frequencies of multiple IgG bands in control patients. This data supports the independence assumption for IgG Western blot bands in controls. "NS" means not significant.

Further demonstration of the use of the above algorithm for IgM Western blot analysis is provided below.

The minimum CDC band criteria for determining a positive IgM Western blot were used for this analysis (i.e., positive 24- and 41-kDa bands with a negative 39-kDa band). It can be deduced that the frequency of a given band pattern cannot be more frequent that that of its least frequent component. Since the 39-kDa band was absent in 16% of the persons with Lyme Disease studied by Engstrom et al., this value represents an upper bound of the true frequency of the minimum criteria.

Because the sample size in the study by Engstrom et al. was small, additional analysis was undertaken to estimate the degree of error in the posttest probability results. To derive an upper-bound estimate for the posttest probability of a given Western blot band pattern, 90% confidence intervals (CIs) were calculated for the involved variables using either a normal distribution or a binomial distribution, depending on the sample size. The upper-bound estimate for the posttest probability was determined by using the highest band pattern frequency among Lyme Disease patients and the lowest band frequencies among controls.

The probability that the 24- and 41-kDa bands will occur together in Lyme Disease patients without the 39-kDa band is at most 0.16 (90% of CI, 0–0.32). The 90% CIs for the 24-, 39-, and 41-kDa band frequencies among controls are 0.358–0.520, 0.026–0.108, and 0.045–0.141, respectively. By use of the above algorithm, the posttest probability of Lyme Disease as a function of the pretest probability is illustrated in FIG. 1. For self-referred persons from areas in which Lyme Disease is highly endemic with atypical symptoms (e.g., myalgias and fatigue), the prior probability of Lyme Disease may be at most 1%–3%. In this low-risk setting, the posttest probability of Lyme Disease may be only 4%–10%, even though both the EIA and Western blot IgM assay are positive (FIG. 1). Even if one assumes test performance favoring the 90% upper-found estimate, post-test probabilities of only 18%–36% are generated. Given that 2.8 million Lyme serologic tests are performed annually in the United States and that fewer than 20,000 cases are reported, it is likely that most testing is done in a low-risk setting. Assuming the data collected by Engstrom et al. are correct, pretest probabilities of ≧20% are needed to generate posttest probabilities of ≧50%. Even when the most favorable assumptions about test performance are used, it is likely that the pretest probability should be ≧5% to generate posttest probabilities of ≧50%.

Positive EIA serology alone does not appear to increase the pre-Western blot probability to >10% in persons with a low pretest risk. Assuming a 10% risk of disease, a minimally positive IgM Western blot result may increase the posttest probability to 32% (see FIG. 1).

However, for certain disease states, such as rheumatoid arthritis and syphilis, Ledue et al. demonstrated a significant correlation among false-positive bands, limiting the specificity of the blot. This caveat must be included in the interpretation of the results. Since the clinical presentation of these cross-reacting conditions is often different from Lyme Disease and since cheap and accurate screening tests for these conditions exist, it should be possible for the clinician to exclude these conditions as causes of false-positive tests.

In summary, the chance that a given patient's Western blot represents active Lyme Disease depends on the prior probability of the disease in that individual as estimated by the physician, the ELISA results if available, the specific band pattern observed and the performance characteristics of the specific Western blot assay used. The prior probability of disease will depend on the patient's clinical signs and symptoms as well as the geographic location of the patient. An example of the specific application of the above algorithm can be demonstrated by using the data derived from the study by Engstrom et al. The frequency of IgM Western blot bands for patients known to be positive for early Lyme Disease by clinical and ELISA criteria and for normal control patients from non-endemic area were utilized. Using the algorithm of the present invention, the posttest probability of the minimum CDC IgM Western blot band criteria is demonstrated by FIG. 1. The current CDC guidelines for IgM Western blot interpretation may yield a substantial number of false-positive results for patients at lower risk of disease (10% or less). Thus, the value of the algorithm in improving the specificity of the diagnosis of early Lyme Disease is demonstrated.

When applied to IgG Western blot tests the algorithm improves the sensitivity of the blot for late Lyme Disease compared to current CDC guidelines. When applied to the data set from the study by Ledue et al. the band frequencies for the IgG Western blot were calculated from pooled data that included both ELISA-positive and ELISA-negative individuals with late Lyme Disease. I felt that accurate data regarding Band Frequencies in the ELISA-negative group could not be generated due to too few ELISA-negative patients in this data set. In the Ledue study a nationally recognized group of sera from 41 patients known to have Lyme Disease collected at least four weeks after onset of illness by the CDC and College of American Pathologists were evaluated using the current CDC methodology and interpretive standards for the Western blot. This collection of sera has been used for quality control purposes across the country. These patients often had a history of erythema migrans or positive cultures for *Borrelia burgdorferi*. The Western blot band pattern for each patient was known and therefore it was possible to calculate the probability of late Lyme Disease for each patient's serum sample using the above algorithm. For this analysis, an immunoblot must demonstrate at least three positive IgG bands and a post test probability of ≧50% in order to call a sample positive. Based on case histories provided by the CDC (M. Schriefer, personal communication), all patients were at either moderate (19%) or high (67%) risk of Lyme disease. If one assumes a pretest probability of ≧5%, then 30/41 late Lyme Disease sera (73%) were positive using the algorithm compared to 18/41 (43.9%) by CDC criteria (Chi-squared 6.08, P<0.025). There was no loss of specificity (100%) when applied to the normal or disease control sera from this data set. Given only modest suspicion of disease, it is demonstrated that the algorithm substantially increases the sensitivity of the Western blot for late Lyme Disease without loss of specificity.

In summary, the Western blot is viewed as multiple tests performed in parallel, some yielding positive results and others yielding negative results. The probability that a given patient's Western blot represents Lyme Disease is calculated from the specific band pattern observed, the pre-test probability of disease, and the performance characteristics of the individual Western blot assay used.

By providing the physician with a tool to estimate the pretest risk of Lyme Disease and combining this estimate with the algorithm, a more accurate diagnosis is permitted. Using the algorithm the physician can diagnose late Lyme Disease with fewer bands than the currently required five bands by CDC, particularly in patients at higher risk of disease. In patients at lower risk of disease, the algorithm improves the specificity of the IgM Western blot for early disease.

Clinical Application of the Invention

When a patient's serum is submitted to a testing laboratory for analysis, specimens can be labelled as early (less than 4 weeks duration) or late Lyme Disease (greater than or equal to 4 weeks duration). It is a common practice for the laboratory to run both the ELISA and Western blot for both IgG and IgM antibodies. The report submitted to the physician should consist of two parts. The first part should ask the physician to assign a pre-test probability of disease using the previously described point system. The second part of the report will contain the probability information derived from the individual patient's Western blot and ELISA data via a computer generated calculation from the reporting laboratory. A separate report will be issued for the IgG and IgM Western blot, providing the post-test probabilities given low, medium, or high suspicion of Lyme Disease. Separate reports can be issued in case the patient has received Lyme Disease vaccine in the past.

For patients with low pretest risk (<7 points), the value of testing is less certain and even positive results can represent past exposure or cross-reacting conditions. Clinical judgement is needed for this assessment. Given moderate to high pre-test risk, and a post-test probability $\geq 50\%$, Lyme Disease is likely. Some false-positive tests may occur with other conditions such as syphilis, infectious mononucleosis, rheumatoid arthritis, systemic lupus erythematosis, and tick-borne relapsing fever. Additional testing may be required to rule out these conditions if clinically warranted. If the posttest probability is less than 50%, then Lyme Disease is unlikely, but could be falsely-negative if tested very early in the course of the illness. Repeat testing within 14–28 days can be warranted if there is still a strong clinical suspicion of disease. For early Lyme Disease, a diagnosis may be made by either the IgG or IgM Western blot. For disease of greater than 4 weeks duration, more reliance should be placed on the IgG Western blot. The IgM Western blot is of limited diagnostic value if it is the only positive test in a patient presenting with late disease. The clinician should rely more on clinical than laboratory criteria in patients who have been extensively pretreated with antibiotics, since treatment may abort a typical antibody response.

Some patients are tested for Lyme disease by both an ELISA and Western blot method. Western blot bands appear more frequently in patients with a positive ELISA test. Through studies, the frequency of a given Western blot band pattern needs to be determined for both Lyme disease patients and controls who are positive by ELISA, and for both patients and controls who are negative by ELISA.

Figure 2:
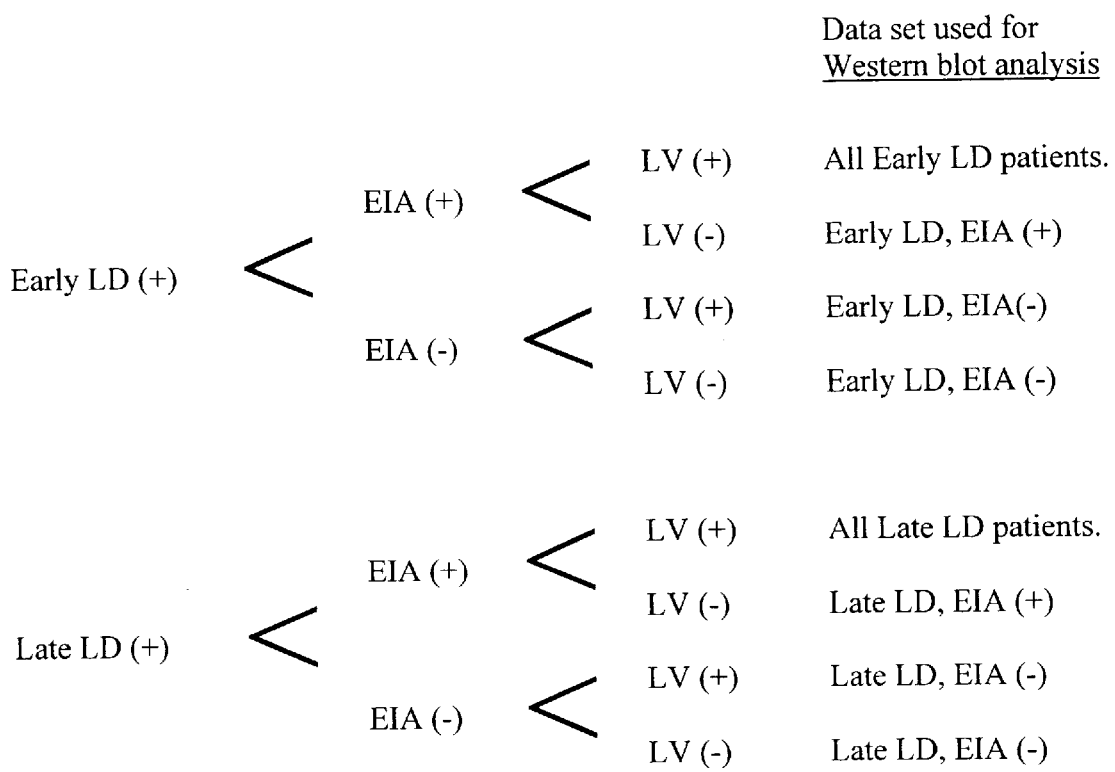
FIG. 2 is a scheme for the data analysis for determining the likelihood that a patient has Lyme Disease when an ELISA assay may be available and when the patient may have had a Lyme Disease vaccine vaccination.

Lyme vaccine will result in a greater frequency of certain bands in vaccinated patients than unvaccinated controls. When using the Western blot for diagnostic purposes, those bands may not be considered in evaluating the Western blot of patients with Lyme disease. A total of six sets of data are used to evaluate serology based on the duration of illness (early vs. later), the ELISA status of the patient (positive or negative), and whether the patient has been vaccinated against Lyme Disease (see FIG. 2).

Those who have received the Lyme Disease vaccine are evaluated by Western blot, ignoring those bands significantly associated with vaccination in control patients (usually 18, 31, 34, and 58 kDa bands). All other patients are evaluated using data derived from patients with both early and late Lyme disease, broken down into those who are ELISA positive and those who are ELISA negative.

In the event that an ELISA is not done, then the data set used to determine band frequency will be either all early Lyme disease patients, or all later Lyme disease patients, based on the duration of illness. See FIG. 2.

References

1) Rahn DW, Evans J (Ed.). Lyme disease. Philadelphia: American College of Physicians, 1998.
2) Sivak SL, et al. Accuracy of immunoblotting to confirm the clinical diagnosis of early Lyme disease. Arch Intern Med 1996; 156-2105–9.
3) Seltzer EG, et al. Misdiagnosis of Lyme disease: when not to order serologic tests. Pediatr Infect Dis J 1996; 15:762–3.
4) Tugwell P, et al. Laboratory evaluation in the diagnosis of Lyme disease. Ann Intern Med 1997; 127:1109–23.
5) Huppertz HI, et al. Diagnosis of paediatric Lyme arthritis using a clinical score. Eur J Pediatr 1998; 157:304–8.
6) Blaauw I, et al. Rational diagnosis and treatment in unclassified arthritis: how clinical data may guide requests for Lyme serology and antibiotic treatment. Ann Rheum Dis 1993; 52-206–210.
7) Centers for Disease Control and Prevention. Case definitions for public health surveillance. MMWR. 1990; 39(RR-13):19–21.
8) Hilton E, et al. Is history useful in the diagnosis of Lyme borreliosis? Infect Dis Clin Pract 1994; 3:277–81.
9) Shadick NA, et al. The long-term clinical outcomes of Lyme disease: a population—based retrospective cohort study. Ann Intern Med 1994; 121:560–7.
10) Blaauw I, et al. Diagnostic tools in Lyme borreliosis: clinical history compared with serology. J Clin Epidemiol 1992; 45:1229–36.
11) Steere AC, et al. The overdiagnosis of Lyme disease. JAMA 1993; 269:1812–6.
12) Kindstrand E. Lyme borreliosis and cranial neuropathy. J Neurol 1995; 242:658–63.
13) Ledue TB, et al. New laboratory guidelines for serologic diagnosis of Lyme disease: evaluation of the two-test protocol. J Clin Minobiol 1996; 34:2343–50.
14) Dressler F, et al. Western blotting in the serodiagnosis of Lyme disease. J Infect Dis 1993; 167:392–400.
15) Fawcett, PT, et al. Frequency and Specificity of Antibodies that Crossreact with *Borrelia burgdorfei* Antigens. J Rheum 1992; 19:582–587.
16) Porwancher, R. A Reanalysis of IgM Western Blot Criteria for the Diagnosis of Early Lyme Disease. J Infect Dis 1999; 179:1021–1024.

APPENDIX

Given: i, k$\in J$ of size n, $B_i/L$ is the ith Western blot band given Lyme disease is present, $B_i/L=B_k/L$ when i=k, $P(B_i) \neq 0$, $L \cap B_i \neq \emptyset$, and $P(B_i/L)$ is significantly greater than $P(B_i/L')$ ($P \leq 0.01$ for each i$\in$J).

If it is assumed that Western blot bands $B_i/L'$ are independent, then one may compute the expected frequency of $\geq 2$ false-positive bands occurring in controls as follows:

1. The chance that $\geq 1$ bands will be positive in controls can be computed as $$1 - \prod_{i \in J} [1 - P(B_i/L')].$$

2. The chance that exactly 1 band will be positive in controls will be found by using the formula:

$$\sum_{i \in J} \frac{P(B_i/L') \times \prod_{k=1}^{n} [1 - P(B_k/L')]}{[1 - P(B_i/L')]}$$

3. Finally, subtracting the value derived from the formula in 2 from the value derived from the formula in 1 yields the chance that $\geq 2$ bands will be seen in controls.

What is claimed is:

1. A method of determining the probability that a patient has Lyme disease by interpreting the results of an immunoassay which measures individual antibody responses to multiple separate antigens associated with Lyme Disease (L) comprising (a) employing scored clinical criteria to obtain a patient's pretest probability of having the disease, (b) carrying out an immunoassay on the patient's body fluid, and, (c) interpreting the results of the immunoassay through an algorithm wherein each individual antibody response is viewed as a separate test performed in parallel, wherein the posttest probability that the patient has Lyme disease is derived as a consequence of the pretest probability that the patient has Lyme disease and the exact combination of antibody responses as measured by the immunoassay as follows:

given that i, j, k∈$\mathcal{J}$ of size n, but i≠k, P(L) is the prior probability of Lyme Disease, P($B_j$/L) is the probability of the jth immunoassay response, $B_j$, given Lyme Disease is present; $B_i$ is the ith antibody response; $B_k$ is the kth antibody response; $B_1B_2=B_1 \cap B_2$, P($B_j$)≠0, L∩$B_j$≠∅, and P($B_j$/L) is significantly greater than P($B_j$/L') (P<0.01 for each j∈J); then the post-test probability that the results of a given patient's immunoassay indicate infection with Lyme Disease is determined using the following formula:

$$\frac{P(B_i \ldots B_j B'_{j+1} \ldots B'_n / L) \times P(L)}{P(B_i \ldots B_j B'_{j+1} \ldots B'_n / L) \times P(L) + \left[\prod_{i=1}^{j} P(B_i / L')\right] \times \left[\prod_{k=j+1}^{n} P(B'_k / L')\right] \times P(L')}$$

and wherein:

$B_1, \ldots, B_n$ represents a group of antibody responses measured by the immunoassay which are associated with infection with Lyme Disease and measured by the immunoassay test for a given patient;

$B_1, \ldots, B_j$ represents those antibody responses included in $B_1, \ldots, B_n$ which are present in the results of a given immunoassay;

$B'_{j+1}, \ldots, B'_n$ represents those antibody responses included in $B_1, \ldots, B_n$ which are not present in the results of a given immunoassay;

P($B_1 \ldots B_j B'_{j+1} \ldots B'_n$/L) represents the frequency that a given immunoassay pattern is present in patients with Lyme Disease;

P($B_i$/L') represents the frequency with which the antibody response, $B_i$ appears in the immunoassay when there is no infection with Lyme Disease;

$$\left[\prod_{i=1}^{j} P(B_i / L')\right]$$

represents the product of the frequencies with which the individual antibody responses present in the given immunoassay pattern appear in the immunoassay when there is no infection with Lyme Disease;

P($B'_k$/L') represents the frequency with which a antibody response, $B_k$ is absent in the immunoassay when there is no infection with Lyme Disease (i≠k), $$\left[\prod_{k=j+1}^{n} P(B'_k / L')\right]$$

represents the product of the frequencies with which the individual antibody responses not present in the immunoassay pattern are absent in the immunoassay when there is no infection with Lyme Disease; and, P(L') represents a pre-test probability of no infection with Lyme Disease.

2. The method of claim 1, wherein P($B_1 \ldots B_j B'_{j+1} \ldots B'_n$/L) is determined by studying the immunoassay patterns of patients with Lyme Disease.

3. The method of claim 1, where P($B_1 \ldots B_j B'_{j+1} \ldots B'_n$/L) is not available through an existing data set, employing the estimation that wherein P($B_1 \ldots B_j B'_{j+1} \ldots B'_n$/L) is less than or equal to P($B_m$/L), where P($B_m$/L) represents the smallest of P($B_i$/L) where i=1, 2, . . . , j and P($B'_k$/L) where k=j+1, . . . , n, and i≠k, and wherein P($B_1 \ldots B_j B'_{j+1} \ldots B'_n$/L) is greater than or equal to $$\left[\prod_{i=1}^{j} P(B_i / L)\right] \times \left[\prod_{k=j+1}^{n} P(B'_k / L)\right].$$

4. The method of claim 1 wherein P(L) is determined using a patient point score.

5. The method of claim 4, wherein P(L) is determined as follows:

(a) a point score is determined for a given patient, as follows:
  (i) add four (4) points if the patient was exposed to wooded, bushy, or grassy areas in a county in which Lyme Disease has been frequently diagnosed;
  (ii) add six (6) points if the patient suffers from unexplained arthritis in a few joints, often relapsing;
  (iii) add six (6) points if the patient suffers from unexplained, acute onset high grade atrioventricular cardiac conduction defects;
  (iv) add six (6) points if the patient suffers from unexplained Bell's palsy, radiculopathy, or peripheral neuropathy;
  (v) add six (6) points if the patient reports a rash compatible with Erythema migrans;
  (vi) add two (2) points if the patient was bitten by a deer tick;
  (vii) add one (1) point if the patient suffers from generalized joint pain or myalgias;
  (viii) add one (1) point if the patient suffers from numbness, concentration difficulty, or memory loss;
  (ix) add 6 points if patient has aseptic meningitis or encephalitis; and
  (x) add one point if a patient has a headache plus either fever or neck stiffness;

(b) P(L) is determined from the point score as follows:
  (i) if the point score is at least fourteen (14) points, P(L)=64%;
  (ii) if the point score is at least seven (7) points but no more than thirteen (13) points, P(L)=19%;
  (iii) if the point score is less than seven (7) points, P(L)=7%.

6. The method of claim 1, wherein P(L')=1−P(L).

7. The method of claim 1, wherein the immunoassay test is performed for IgG, or IgM antibody.

8. A method of claim 1, wherein the disease is late Lyme Disease.

9. The method of claim 8, wherein the probability is determined as follows:

Given that i, j, k∈$\mathcal{J}$ of size n, but i≠k, P(L) is the prior probability of late Lyme Disease, P($B_j$/L) is the probability of the jth antibody response, $B_j$, given late Lyme Disease is present; $B_i$ is the ith antibody response; $B_k$ is the kth antibody response; $B_1B_2=B_1 \cap B_2$, P($B_j$)≠0, L∩$B_j$≠∅, and P($B_j$/L) is significantly greater than P($B_j$/L') (P<0.01 for each j∈J); then the post-test probability that the results of the immunoassay test indicate infection with late Lyme Disease is determined using the following formula:

$$\frac{P(B_i \ldots B_j B'_{j+1} \ldots B'_n / L) \times P(L)}{\begin{array}{c} P(B_i \ldots B_j B'_{j+1} \ldots B'_n / L) \times \\ P(L) + \left[\prod_{i=1}^{j} P(B_i / L')\right] \times \left[\prod_{k=j+1}^{n} P(B'_k / L')\right] \times P(L') \end{array}}$$

and wherein:
- $B_1, \ldots, B_n$ represents a group of antibody responses measure by the immunoassay which are associated with infection with late Lyme Disease and measured by the immunoassay test for a given patient;
- $B_1, \ldots, B_j$ represents those antibody responses included in $B_1, \ldots, B_n$ which are present in the results of a given immunoassay;
- $B'_{j+1}, \ldots, B'_n$ represents those antibody responses included in $B_1, \ldots, B_n$ which are not present in the results of a given immunoassay;
- $P(B_1 \ldots B_j B'_{j+1} \ldots B'_n/L)$ represents the frequency that a given immunoassay pattern is present in patients with Lyme Disease;
- $P(B_i/L')$ represents the frequency with which the antibody response, $B_i$, appears in the immunoassay when there is no infection with Lyme Disease;

$$\left[\prod_{i=1}^{j} P(B_i / L')\right]$$

represents the product of the frequencies with which the individual antibody responses present in the given immunoassay pattern appear in the immunoassay when there is no infection with Lyme Disease;

$P(B'_k/L')$ represents the frequency with which a antibody response, $B_k$, is absent in the immunoassay when there is no infection with Lyme Disease ($i \neq k$), $$\left[\prod_{k=j+1}^{n} P(B'_k / L')\right]$$

represents the product of the frequencies with which the individual antibody responses not present in the immunoassay pattern are absent in the immunoassay when there is no infection with Lyme Disease; and, $P(L')$ represents the pre-test probability of no infection with Lyme Disease.

10. The method of claim 9, wherein $P(B_1 \ldots B_j B'_{j+1} \ldots B'_n/L)$ is determined by studying the immunoassay patterns of patients with late Lyme Disease.

11. The method of claim 9, where $P(B_1 \ldots B_j B'_{j+1} \ldots B'_n/L)$ is not available through an existing data set, employing the estimation that wherein $P(B_1 \ldots B_j B'_{j+1} \ldots B'_n/L)$ is less than or equal to $P(B_m L)$, where $P(B_m/L)$ represents the smallest of $P(B_i/L)$ where $i=1, 2, \ldots, j$ and $P(B'_k/L)$ where $k=j+1, \ldots, n$, and $i \neq k$, and wherein $P(B_1 \ldots B_j B'_{j+1} \ldots B'_n/L)$ is greater than or equal to $$\left[\prod_{i=1}^{j} P(B_i / L)\right] \times \left[\prod_{k=j+1}^{n} P(B'_k / L)\right].$$

12. The method of claim 9 wherein $P(L)$ is determined using a patient point score.

13. The method of claim 12, wherein $P(L)$ is determined as follows:
   (a) a patient point score is determined for a given patient, as follows:
      (i) add four (4) points if the patient was exposed to wooded, bushy, or grassy areas in a county in which Lyme Disease has been frequently diagnosed;
      (ii) add six (6) points if the patient suffers from unexplained arthritis in a few joints, often relapsing;
      (iii) add six (6) points if the patient suffers from unexplained, acute onset high grade atrioventricular cardiac conduction defects;
      (iv) add six (6) points if the patient suffers from unexplained Bell's palsy, radiculopathy, or peripheral neuropathy;
      (v) add six (6) points if the patient reports a rash compatible with Erythema migrans;
      (vi) add two (2) points if the patient was bitten by a deer tick;
      (vii) add one (1) point if the patient suffers from generalized joint pain or myalgias;
      (viii) add one (1) point if the patient suffers from numbness, concentration difficulty, or memory loss;
      (ix) Add six (6) points if the patient has aseptic meningitis or encephalitis; and
      (x) Add one point if the patient has headache plus either fever or neck stiffness;
   (b) $P(L)$ is derived from the point score as follows:
      (i) if the point score is at least fourteen (14) points, $P(L)=64\%$;
      (ii) if the point score is at least seven (7) but not more than thirteen (13) points, $P(L)=19\%$;
      (iii) if the point score is less than 7 points, $P(L)=7\%$.

14. The method of claim 9, wherein $P(L')=1 \, P(L)$.

15. The method of claim 9, where the immunoassay is performed for IgG or IgM antibody.

16. The method of claim 9, wherein the immunoassay is a Western blot.

17. The method of claim 1 wherein the disease is early Lyme Disease.

18. The method of claim 17, wherein the probability is determined as follows:
   Given that $i, j, k \in J$ of size n, but $i \neq k$, $P(L)$ is the prior probability of early Lyme Disease, $P(B_j/L)$ is the probability of the jth antibody response, $B_j$, given early Lyme Disease is present; $B_i$ is the ith antibody response; $B_k$ is the kth antibody response; $B_1 B_2 = B_1 \cap B_2$, $P(B_j) \neq 0$, $L \cap B_j \neq \emptyset$, and $P(B_j/L)$ is significantly greater than $P(B_j/L')$ ($P<0.01$ for each $j \in J$); then the post-test probability that the results of the immunoassay test indicate infection with early Lyme Disease is determined using the following formula:

$$\frac{P(B_i \ldots B_j B'_{j+1} \ldots B'_n / L) \times P(L)}{\begin{array}{c} P(B_i \ldots B_j B'_{j+1} \ldots B'_n / L) \times \\ P(L) + \left[\prod_{i=1}^{j} P(B_i / L')\right] \times \left[\prod_{k=j+1}^{n} P(B'_k / L')\right] \times P(L') \end{array}}$$

and wherein:
- $B_1, \ldots, B_n$ represents a group of antibody responses measure by the immunoassay which are associated with infection with early Lyme Disease and measured by the immunoassay test for a given patient;
- $B_1, \ldots, B_j$ represents those antibody responses included in $B_1, \ldots, B_n$ which are present in the results of a given immunoassay;

$B'_{j+1}, \ldots, B'_n$ represents those antibody responses included in $B_1, \ldots, B_n$ which are not present in the results of a given immunoassay;

$P(B_1 \ldots B_j B'_{j+1} \ldots B'_n/L)$ represents the frequency that a given immunoassay pattern is present in patients with early Lyme Disease;

$P(B_i/L')$ represents the frequency with which the antibody response, $B_i$, appears in the immunoassays when there is no infection with Lyme Disease;

$$\left[\prod_{i=1}^{j} P(B_i/L')\right]$$

represents the product of the frequencies with which the individual antibody responses present in the given immunoassay pattern appear in the immunoassay when there is no infection with Lyme Disease;

$P(B'_k/L')$ represents the frequency with which a antibody response, $B_k$, is absent in the immunoassays when there is no infection with Lyme Disease ($i \neq k$)

$$\left[\prod_{k=j+1}^{n} P(B'_k/L')\right]$$

represents the product of the frequencies with which the individual antibody responses not present in the immunoassay pattern are absent in the immunoassays when there is no infection with Lyme Disease; and, $P(L')$ represents a pre-test probability of no infection with Lyme Disease.

19. The method of claim 18 where P(L) is determined using a patient point score.

20. The method of claim 19 where P(L) is determined as follows:
  (a) a point score is determined for a given patient, as follows:
    (i) add four (4) points if the patient was exposed to wooded, bushy, or grassy areas in a county in which Lyme Disease has been frequently diagnosed;
    (ii) add six (6) points if the patient suffers from unexplained arthritis in a few joints, often relapsing;
    (iii) add six (6) points if the patient suffers from unexplained, acute onset high grade atrioventricular cardiac conduction defects;
    (iv) add six (6) points if the patient suffers from unexplained Bell's palsy, radiculopathy, or peripheral neuropathy;
    (v) add six (6) points if the patient reports a rash compatible with Erythema migrans;
    (vi) add two (2) points if the patient was bitten by a deer tick;
    (vii) add one (1) point if the patient suffers from generalized joint pain or myalgias;
    (viii) add one (1) point if the patient suffers from numbness, concentration difficulty, or memory loss;
    (ix) add six (6) points if the patient has aseptic meningitis or encephalitis; and
    (x) add one (1) point if the patient has headache plus either fever or neck stiffness;
  (b) P(L) is derived from the point score as follows:
    (i) if the point score is at least fourteen (14) points, P(L)=64%;
    (ii) if the point score is at least seven (7) but not more than thirteen (13) points, P(L)=19%;
    (iii) if the point score is less than seven (7) points, P(L)=7%.

21. The method of claim 18, wherein $P(B_1 \ldots B_j B'_{j+1} \ldots B'_n/L)$ is determined by studying the immunoassay patterns of patients with early Lyme Disease.

22. The method of claim 18, where $P(B_1 \ldots B_j B'_{j+1} \ldots B'_n/L)$ is not available through an existing data set, employing the estimation that wherein $P(B_1 \ldots B_j B'_{j+1} \ldots B'_n/L)$ is less than or equal to $P(B_m/L)$, where $P(B_m/L)$ represents the smallest of $P(B_i/L)$ where $i=1, 2, \ldots, j$ and $P(B'_k/L)$ where $k=j+1, \ldots, n$, and $i \neq k$, and wherein $P(B_1 \ldots B_j B'_{j+1} \ldots B'_n/L)$ is greater than or equal to $$\left[\prod_{i=1}^{j} P(B_i/L)\right] \times \left[\prod_{k=j+1}^{n} P(B'_k/L)\right].$$

23. The method of claim 16, wherein the immunoassay is performed for IgG or IgM antibody.

24. The method of claim 1 wherein the immunoassay is a Western blot.

25. The method of claim 18, wherein the immunoassay is a Western blot.

26. A method of determining the probability that a patient has Lyme disease by interpreting the results of a Western blot which measures individual antibody responses to multiple separate antigens associated with Lyme Disease (L) comprising (a) employing scored clinical criteria to obtain a patient's pretest probability of having the disease, (b) carrying out a Western blot on the patient's body fluid, and, (c) interpreting the results of the Western blot through an algorithm wherein each individual antibody response is viewed as a separate test performed in parallel, and wherein the posttest probability that the patient has Lyme disease is derived as a consequence of the pretest probability that the patient has Lyme disease and the exact combination of antibody responses as measured by the Western blot.

* * * * *